(12) United States Patent
Otsubo

(10) Patent No.: US 6,450,996 B1
(45) Date of Patent: Sep. 17, 2002

(54) DISPOSABLE DIAPER

(75) Inventor: Toshifumi Otsubo, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/467,714

(22) Filed: Dec. 21, 1999

(30) Foreign Application Priority Data

Dec. 25, 1998 (JP) .......................................... 10-371158

(51) Int. Cl.⁷ ................................................ A61F 13/15
(52) U.S. Cl. ................. 604/385.01; 604/365; 604/364; 604/395; 604/385.14; 128/287
(58) Field of Search ....................... 604/385.14, 385.05, 604/385.13, 385.04, 385.01, 385.11, 378, 327, 389, 391, 385.21

(56) References Cited

U.S. PATENT DOCUMENTS

| 3,667,466 A | * | 6/1972 | Ralph .......................... 128/287 |
| 3,771,524 A | | 11/1973 | Ralph |
| 4,022,210 A | | 5/1977 | Glassman |
| 4,036,234 A | * | 7/1977 | Ishizuka ...................... 128/287 |
| 4,210,143 A | * | 7/1980 | De Jonckheere ............ 128/287 |
| 4,265,245 A | | 5/1981 | Glassman |
| 4,964,857 A | * | 10/1990 | Osborn ......................... 604/395 |
| 5,160,331 A | * | 11/1992 | Forester ....................... 604/364 |
| 5,236,428 A | | 8/1993 | Zajaczkowski |
| 5,613,959 A | * | 3/1997 | Roessler ....................... 604/364 |
| 6,049,023 A | * | 4/2000 | Blenke ......................... 604/365 |
| 6,193,701 B1 | * | 2/2001 | Van Gompel .......... 604/385.01 |
| 6,254,583 B1 | * | 7/2001 | Coates ................... 604/385.14 |

FOREIGN PATENT DOCUMENTS

| GB | 1 574 234 | 9/1980 |
| GB | 2 526 803 | 12/1992 |
| JP | 61-28002 | 2/1986 |
| JP | 5-3889 | 1/1993 |
| JP | 5-33717 | 5/1993 |
| JP | 7-31022 | 6/1995 |

* cited by examiner

Primary Examiner—John J. Calvert
Assistant Examiner—Angela J. Grayson
(74) Attorney, Agent, or Firm—Baker & Daniels

(57) ABSTRACT

A disposable diaper includes transversely opposite side edge regions thereof and the side edge regions are folded to form pleats each presenting a Z-shaped cross section and an body waste disposal sheet is bonded along its transversely opposite side edge regions to upper surfaces of the pleats so that the disposal sheet may be separated from the diaper as the transversely opposite side edge regions of the diaper are held and bilaterally pulled by a person having charge of body waste disposal with his or her hands.

7 Claims, 2 Drawing Sheets

DISPOSABLE DIAPER

BACKGROUND OF THE INVENTION

The present invention relates to a disposable diaper and more particularly to such a diaper having means facilitating disposal of body waste discharged on the diaper.

Disposable diapers including a body waste disposal sheet separably bonded to a topsheet defining a skin-contacting surface of the diaper so that the disposable diaper itself and body waste discharged thereon may be separately dealt with is disclosed, in Japanese Patent Application Disclosure Gazette (Kokai) Nos. Sho61-28002 and Hei5-3889, and Japanese Utility Model Application Disclosure (Kokai) Nos. Hei7-31022 and Hei5-33717.

The diapers disclosed in these publications are adapted to separate the body waste disposal sheets from the diapers and then to wrap body waste discharged on the disposal sheets with the latter before throwing the disposal sheet and body waste discharged thereon away in a predetermined container or equipment, or adapted to throw them away into a bowl of flush toilet, as long as the body waste disposal sheet is water-dispersible. From the viewpoint of public sanitation, the latter case is preferred to the former case in which body waste discharged on the disposal sheet is throw away directly into a predetermined container or equipment.

However, independently of whether the disposal sheet is thrown away together with body waste discharged thereon into a predetermined container or equipment or into a bowl of flush toilet, these known diapers require the person having charge of body waste disposal to separate the disposal sheet from the diapers by holding the disposal with his or her hands. Holding the disposal sheet directly by holding with the hands is apt to smear the hands of the person having charge of body waste disposal with body waste. Consequently, the person having charge of body waste disposal must wash his or her hands every time he or she handles body waste discharged on the disposal sheet.

SUMMARY OF THE INVENTION

It is an object of the present invention to provide a disposable diaper including an body waste disposal sheet adapted to be separable from the diaper without holding the disposal sheet directly with the hands of a person having charge of body waste disposal.

According to the present invention, there is provided a disposable diaper comprising an absorbent unit including a liquid-pervious topsheet, a liquid-impervious backsheet and a liquid-absorbent core disposed between the topsheet and the backsheet to define a longitudinal center line, a front waist region, a rear waist region and a crotch region, and a body waste disposal sheet separably bonded at least to the crotch region.

The disposable diaper of the present invention includes an absorbent unit being provided along transversely opposite side edge regions thereof extending in a longitudinal direction thereof with a pair of pleats each having a Z-shaped cross section and including a lower portion folded toward the longitudinal center line and an upper portion folded outward in the direction opposed to the direction in which the lower portion is folded and the body waste disposal sheet being separably bonded along a transversely opposite side edge regions thereof extending in the longitudinal direction to the upper portions of the respective pleats so that the body wastes disposal sheet is separated from the absorbent unit as the pleats are pulled in opposite directions.

The present invention includes alternative embodiments wherein the body waste disposal sheet is water-dispersible; wherein a bonding strength with which the body waste disposal sheet is bonded along a transversely opposite side edge regions thereof to the upper portions of the pleats, respectively, is lower than a tear strength of the body waste disposal sheet in a transverse direction thereof; wherein the bonding strength is in a range of 30~200 g/25 mm when the body waste disposal sheet is dry and in a range of 20~100 g/25 mm when the body waste disposal sheet is wet; wherein the lower portions of the pleats respectively have a width of 10~60 mm; wherein the pleats are respectively formed by a pair of side flaps extending outward beyond transversely opposite side edges of the absorbent core; and wherein the body waste disposal sheet is bonded to the upper portions of the pleats only in the crotch region so that the pleats in the front and rear waist regions is laterally unfolded without being restrained by the body waste disposal sheet.

DETAILED DESCRIPTION OF THE PREFERRED EMBODIMENTS

Details of a disposable diaper according to the present invention will be more fully understood from the description of embodiments given hereunder with reference to the accompanying drawings.

Figure 1:
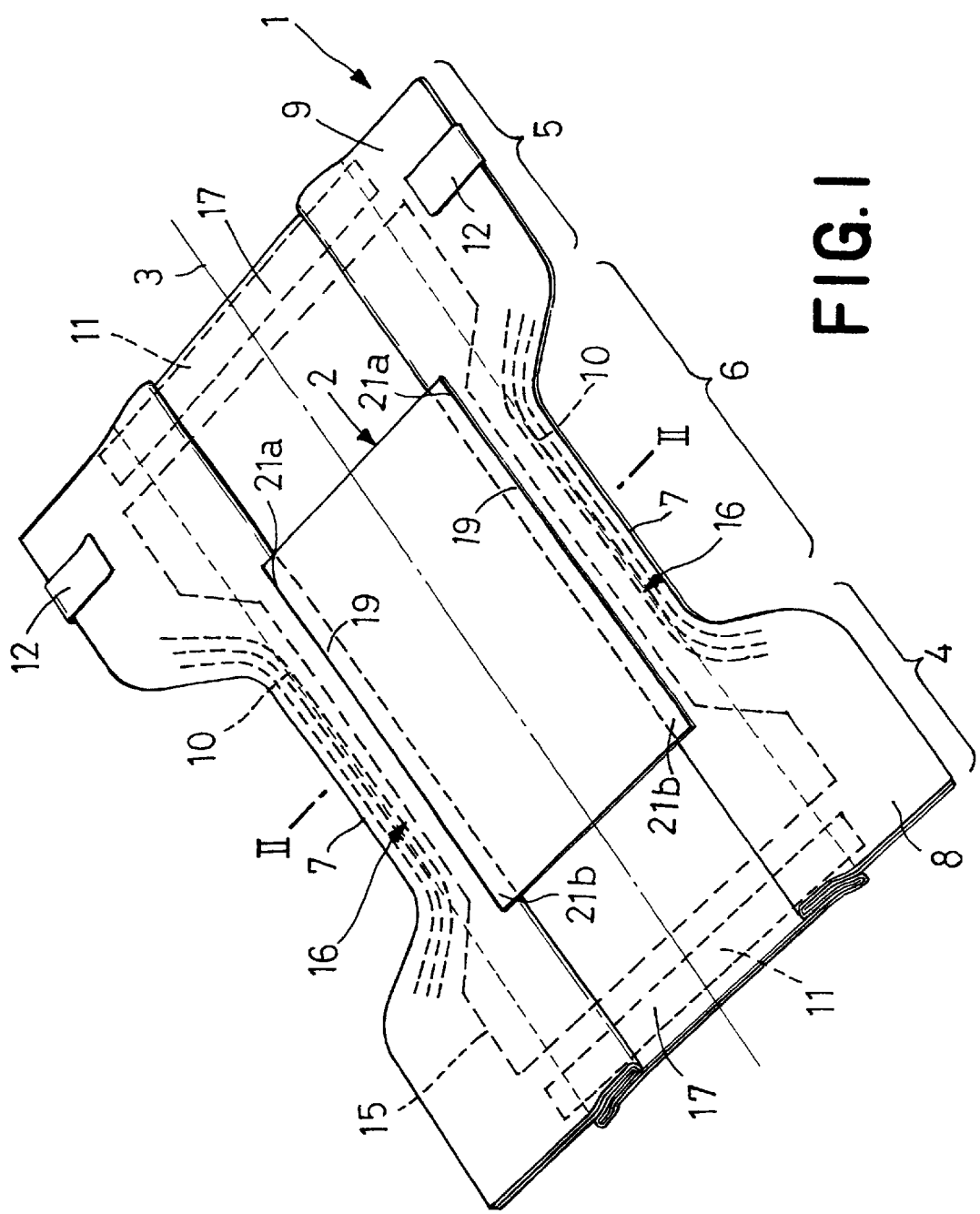
FIG. 1 is a perspective view showing a disposable diaper as viewed from its side intended to come in contact with a wearer's skin.

Referring to FIG. 1, the diaper basically comprises an absorbent unit 1 and an body waste disposal sheet 2. The diaper is bilaterally symmetric about a center line 3 extending in the longitudinal direction and has a front waist region 4, a rear waist region 5 and a crotch region 6 extending between the front and rear waist regions 4, 5. The absorbent unit 1 is formed along transversely opposite side edge s of the crotch region 6 with cutouts 7, 7 intended to encircle the wearer's legs. The cutouts 7, 7 and respective ends 8, 9 of the front and rear waist regions 4, 5 defining waist lines are provided with elastic members 10, 10; 11, 11 each extending in the circumferential direction. Contraction of the elastic members presses the diaper around the wearer's legs and waist, respectively. The rear waist region 5 is provided on its transversely opposite sides with tape fasteners 12, 12. The body waste disposal sheet 2 is laid on the inner surface of the absorbent unit 1 in the crotch region 6.

Figure 2:
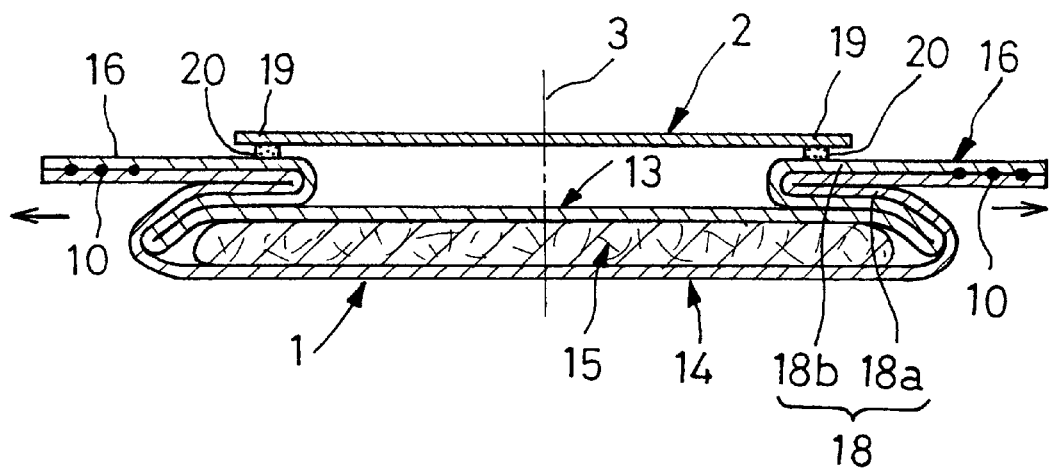
FIG. 2 is a scale-enlarged sectional view taken along a line II—II in FIG. 1.

Referring to FIG. 2, the absorbent unit 1 includes a liquid-pervious topsheet 13, a liquid-impervious backsheet 14, a liquid-absorbent core 15 disposed between these two sheets 13, 14 and a pair of side flaps 16, 16 each including portions of the topsheet 13 and the backsheet 14 extending outward beyond transversely opposite side edges of the absorbent core 15 and bonded together by well known bonding means such as hot melt adhesive (not shown). As will be apparent from FIG. 1, the absorbent unit 1 further includes a pair of end flaps 17, 17 each including portions of the topsheet 13 and the backsheet 14 extending outward beyond longitudinally opposite ends of the absorbent core 15 and bonded together by well known bonding means such as hot melt adhesive (not shown). The absorbent core 15 is semi-rigid and includes an absorbing mechanism of well known art. The absorbent core 15 is substantially fixed between the topsheet 13 and the backsheet 14 using the well known bonding means such as hot melt adhesive (not shown) so that the absorbent core 15 might not easily get out of its initial shape. Both the topsheet 13 and the backsheet 14 have a high flexibility and therefore both the side flaps 16 and the end flaps 17 formed by extensions of the topsheet 13 and the backsheet 14 have a sufficiently high flexibility to fit around the wearer's legs and waist with a desired soft touch. The elastic members 10, 10; 11, 11 are bonded under tension in the longitudinal direction thereof between the topsheet 13 and the backsheet 14 by means of well known hot melt adhesive (not shown).

Referring again to FIG. 2, on each lateral side of the absorbent unit 1, the side flap 16 forms a pleat 18 having a Z-shaped cross section. More specifically, the pleat 18 includes a lower portion 18a folded toward the center line 3 extending longitudinally of the absorbent unit 1 and an upper portion 18b folded outward, i.e., away from the center line 3 and placed upon the upper surface of the lower portion 18a. As has been described with reference to FIG. 1, the body waste disposal sheet 2 is laid upon the surface of the absorbent unit 1 intended to come in contact with the wearer's skin, i.e., upon the upper surface of the topsheet 13. More specifically, the body waste disposal sheet 2 is separably bonded along its transversely opposite side edges 19 to the topsheet 13 defining the upper surface of the upper portions 18b of the pleats 18 by means of bonding spots 20 intermittently arranged in the longitudinal direction of the body waste disposal sheet 2. The bonding means 20 may be formed by well known hot melt adhesive, thermal emboss/deboss or the like and, as will be described later in detail, it is desired that the bonding means 20 should allow the body waste disposal sheet 2 to be easily separated from the absorbent unit 1. Specifically, it is an important feature of the present invention that the body waste disposal sheet 2 should be able to be separated from the upper portions 18b, 18b of the respective pleats 18, 18 as the pleats 18 are pulled and unfolded in opposed directions indicated by respective arrows. An important feature of the present invention basically lies in a novel arrangement such that the transversely opposite side edges 19, 19 of the body waste disposal sheet 2 can be easily separated from the upper portions 18b, 18b of the respective pleats 18, 18 as the pleats 18, 18 are laterally pulled. In another aspect, an important feature of the present invention lies in a unique arrangement making it possible to eliminate any apprehension that the body waste disposal sheet 2 might be torn not only under a tensile force occurring circumferentially of the wearer's torso during use of the diaper but also under a tensile force necessarily exerted thereon when the pleats 18, 18 are unfolded. To achieve this, the bonding means 20 and the body waste disposal sheet 2 are preferably in such a mutual relationship that a bonding strength of the former is lower than a tear strength of the latter in its transverse (width) direction. To establish such relationship, the bonding strength is preferably in a range of 30~100 g/25 mm when the body waste disposal sheet 2 is in dry condition and in a range of 10~100 g/25 mm when the body waste disposal sheet 2 is in wet condition. Assumed that this relationship is established, it is desirable to adjust the bonding strength so as to be highest in regions 21a, 21b extending adjacent the front and rear waist regions, respectively, and lowest in regions defined between the regions 21a, 21b. Such adjustment of the bonding strength advantageously meets the following characteristics: the body waste disposal sheet 2 is prevented from being unintentionally separated from the absorbent unit 1 when the pleats 18, 18 in the front and rear waist regions are unfolded to wear the diaper or during use of the diaper; and the body waste disposal sheet 2 can be easily separated from the absorbent unit 1 as the pleats 18, 18 are unfolded for the purpose of body waste disposal. Operation of unfolding the pleats 18, 18 may be carried out by holding the pleats 18, 18 with both hands, for example, with the fingers of both hands inserted under the respective lower potions 18a, 18a. To make this operation easy, each of the lower portions 18a preferably has a width of 10~60 mm.

In order that the body waste disposal sheet 2 can be thrown into a flush toilet together with body waste discharged thereon without any anxiety, the body waste disposal sheet 2 is preferably made of water-dispersible or water-soluble material. While such material is not required, a sheet obtained by treating staple fibers and/or pulp fibers with suitable water-soluble binder such as PVA or CMC, or a sheet obtained by subjecting pulp fibers to process of paper making is one example as such material. The body waste disposal sheet 2 may have a sufficiently low porosity to prevent loose passage from permeating the sheet. Furthermore, the body waste disposal sheet 2 may have a degree of stretchability so far as the operation of separating the body waste disposal sheet 2 from the upper portions 18b, 18b of the pleats 18, 18 is not obstructed thereby.

While the absorbent unit 1 is illustrated to present the simplest construction, it should be understood that the other various embodiments are possible without departing from the scope of the present invention. For example, both lateral regions of the respective side flaps 16, 16, i.e., the upper portions 18b, 18b of the respective pleats 18, 18 may be provided with a pair of elastic second side flaps (barrier cuffs) normally biased by their elastic contractile force to rise against the wearer's skin. Further, the absorbent unit 1 may be realized in the form of a pants-type diaper (i.e., pull-on-type diaper) by bonding the front and rear waist regions 4, 5 to each other along their transversely opposite side edges.

The topsheet 13 may be formed from a fibrous nonwoven fabric, a porous plastic film or the like, the backsheet 14 may be formed from a moisture-pervious but liquid-impervious plastic film, a laminate of such plastic film and fibrous nonwoven fabric or the like, and the absorbent core 15 may be formed from a mixture of fluff pulp and superabsorbent polymer particles covered with a liquid-absorbent and -diffusive sheet or the like. Thus the components 13, 14, 15 may be formed from the stock materials usually used to form the components of disposable diapers or sanitary napkins.

With the diaper of the present invention constructed as has been described above, the manner of disposal of body waste discharged on the disposal sheet 2 will be different depending on whether the disposal sheet 2 is water-dispersible or not. When sheet 2 is water-dispersible, a person having charge of body waste may, for example, hold the side flaps 16, 16 with or without inserting his or her fingers of both hands under the lower portions 18a, 18a of the pleats 18, 18, respectively, then turn the diaper inside out so that the body waste disposal sheet 2 may face a bowl of the flush toilet, and pull the diaper outward in opposed directions (as indicated by two arrows in FIG. 2) to unfold the pleats 18, 18. Thereupon, the disposal sheet 2 is separated from the absorbent unit 1 and thrown together with body waste discharged thereon into the bowl of the flush toilet. In this case, it is not necessary at all for the person having charge of body waste disposal to touch the disposal sheet 2 with his or her hands and there is no apprehension that the hands of such person might be smeared with body waste . If the disposal sheet 2 is not water-dispersible, the person having charge of body waste disposal may wrap body waste with the disposal sheet 2 after the disposal sheet 2 has been separated from the absorbent unit 1 by the operation of laterally pulling the diaper and thereby unfolding the pleats 18, 18, and then throw away this wrapped body waste into a predetermined container or equipment. In this case, the hands of the person having charge of body waste disposal necessarily contacts the disposal sheet 2. However, operation of wrapping body waste with the disposal sheet 2 which has already been separated from the absorbent unit 1 enables such person to protect his or her hands from being in direct contact with body waste as carefully as possible. On the contrary, it is often difficult for such person to protect his or her hands from being smeared with body waste when the disposal sheet 2 must be separated from the absorbent unit 1 with the disposal sheet 2 held directly by his or her hands.

As will be apparent from the foregoing description, the diaper of the present invention allows the person having charge of body waste disposal to deal with body waste discharged on the disposal sheet without any apprehension that his or her hands might be smeared with body waste. Furthermore, the person having charge of body waste disposal can avoid at least undesirable operation of separating the disposal sheet from the absorbent unit held directly with his or her hands. In this way, disposal of the diaper after a single use is drastically simplified.

In the course of putting the diaper on the wearer's body as well as after the diaper has been put on, the disposal sheet serves to maintain the pleats in the crotch region of the diaper as they are. In other words, the disposal sheet ensures a width of the crotch region to be effectively placed against the crotch of the wearer. In addition, the disposal sheet does not restrain portions of the pleats lying in the front and rear waist regions and allows these portions to be unfolded by a desired dimension so that the front and rear waist regions can be stabilized around the of the wearer with a good appearance.

What is claimed is:

1. A disposable diaper comprising:
    an absorbent unit including:
        a liquid-pervious topsheet;
        a liquid-impervious backsheet; and
        a liquid-absorbent core disposed between the topsheet and the backsheet,
    said absorbent unit having a longitudinal center line, a front waist region, a rear waist region and a crotch region; and
    a body waste disposable sheet removably bonded at least to said crotch region,
    said absorbent unit being provided along transversely opposite side edge regions thereof with a pair of pleats that extend in a longitudinal direction, each of said pair of pleats having a Z-shaped cross section defined by a lower portion folded toward said longitudinal center line and an upper portion folded outward in an opposite direction to the direction in which said lower portion is folded and said body waste disposable sheet is removably bonded along transversely opposite side edge regions thereof extending in the longitudinal direction to said upper portions of the pleats so that said body waste disposal sheet is separated from said absorbent unit when said pleats are pulled in opposite directions.

2. The diaper according to claim 1, wherein said body waste disposal sheet is water-dispersible.

3. The diaper according to claim 1, wherein a bonding strength with which said body waste disposal sheet is bonded along the transversely opposite side edge regions thereof to said upper portions of said pleats, is lower than a tear strength of said body waste disposal sheet in its transverse direction.

4. The diaper according to claim 3, wherein said bonding strength of said body waste disposal sheet to the upper portions of said pleats is in a range of 30~200 g/25 mm when said body waste disposal sheet is dry and is in a range of 20~100 g/25 mm when said body waste disposal sheet is wet.

5. The diaper according to claim 1, wherein said lower portions of said pleats have a width of 10~60 mm.

6. The diaper according to claim 1, wherein said pleats comprise a pair of side flaps that extend outward beyond transversely opposite side edges of said absorbent core.

7. The diaper according to claim 1, wherein said body waste disposal sheet is bonded to said upper portions of said pleats only in said crotch region so that portions of said pleats in said front and rear waist regions may be laterally unfolded without being restrained by the body waste disposal sheet.

* * * * *